(12) United States Patent
Galvan-Garcia

(10) Patent No.: US 9,731,118 B2
(45) Date of Patent: Aug. 15, 2017

(54) ANNULAR ELECTRODE ARRAY

(76) Inventor: Pedro Galvan-Garcia, Palmview, TX (US)

(*) Notice: Subject to any disclaimer, the term of this patent is extended or adjusted under 35 U.S.C. 154(b) by 404 days.

(21) Appl. No.: 13/066,042

(22) Filed: Apr. 5, 2011

(65) Prior Publication Data

US 2012/0259388 A1 Oct. 11, 2012

(51) Int. Cl.
*A61N 1/04* (2006.01)
*A61N 1/05* (2006.01)
*A61N 1/36* (2006.01)

(52) U.S. Cl.
CPC .......... *A61N 1/0556* (2013.01); *A61N 1/0534* (2013.01); *A61N 1/0551* (2013.01); *A61N 1/0558* (2013.01); *A61N 1/36103* (2013.01); *A61N 1/36125* (2013.01)

(58) Field of Classification Search
CPC .... A61N 1/0551; A61N 1/0534; A61N 1/375; A61N 1/0529; A61N 1/3752; A61N 1/3605; A61N 1/36125; A61N 1/0556; A61N 1/36103
USPC ................................................ 607/116, 118
See application file for complete search history.

(56) References Cited

U.S. PATENT DOCUMENTS

| | | | |
|---|---|---|---|
| 5,215,088 A | 6/1993 | Normann | |
| 5,824,027 A * | 10/1998 | Hoffer | A61N 1/0556 600/377 |
| 6,908,470 B2 | 6/2005 | Stieglitz | |
| 6,993,392 B2 | 1/2006 | Nicolelis | |
| 7,058,455 B2 | 6/2006 | Huie | |
| 7,326,649 B2 | 2/2008 | Rodger | |
| 7,603,153 B2 | 10/2009 | Jacobsen | |
| 2010/0211172 A1* | 8/2010 | Bellamkonda | A61B 5/0031 623/11.11 |

OTHER PUBLICATIONS

Branner, Long-term Stimulation and Recording with a Penetrating Microelectrode Array in Cat Sciatic Nerve, IEEE Transactions in Biomedical Engineering1992; 39: 893-902.
Bowman, Acute and Chronic Implantation of Coiled Wire Intraneural Electrodes During Cyclical Electrical Stimulation, Annals of Biomedical Engineering 1985; 13: 75-93.
(Continued)

*Primary Examiner* — Michael Kahelin
*Assistant Examiner* — Minh Duc Pham
(74) *Attorney, Agent, or Firm* — Edwin S. Flores; Chalker Flores, LLP

(57) ABSTRACT

A three-dimensional annular electrode array (AEA) device is disclosed for use as a cybernetic neural interface for the neural control and sensory feedback of a bionic prosthetic device. The AEA, designed for implantation into a nerve, is comprised of a body (6) that can be coupled to a sleeve(s) (9, 10) or a sleeve(s) with a compartmentalized inner core (12) for connection to the proximal and distal ends of a transected nerve, respectively. Regenerating nerve axons capture and sequester laterally projecting electrode terminals (4) arranged in radiating clusters (5) of a plurality of electrode sub-array nodes (2) that make up the array; connected by a primary electrode lead (7) to a connector contact array (3) in a plurality of connectors (1) for connection to wired or wireless electromechanical systems.

14 Claims, 4 Drawing Sheets

(56) References Cited

OTHER PUBLICATIONS

Agnew, Effects of Prolonged Electrical Stimulation of Peripheral nerve, Neural Prostheses: Fundamental Studies, 1990: 147-68, Prentice Hall, Englewood Cliffs.
McNeal, Experience with Implanted Electrodes, Neurosurgery, 1977; 1: 228-229.
Grill, Electrical Properties of Implant Encapsulation Tissue. Annals Biomedical Engineering, 1994; 22: 23-33.
Kovacs, Regeneration Microelectrode Array for Peripheral Nerve Recording and Stimulation, IEEE Transactions in Biomedical Engineering, 1992; 39: 893-9.
Prodanov, Functional Electric Stimulation for Sensory and Motor Functions: Progress and Problems, http://www.diagnosticarea.com/publications/FES_Review.html.
Rutten, Selective Electrical Interfaces with the Nervous System. Annu. Rev. Biomed. Eng. 2002; 4:407-52.
Navarro, A Critical Review of Interfaces with the Peripheral Nervous System for the Control of Neuroprostheses and Hybrid Bionic Systems. J. Periph. Nerv. Sys. 2005; 10:229-58.
Bellamkonda, Materials for Neural Interfaces. MRS Bulletin, 2012; 37:557-61.
Akhil Srinivasan et al., Microchannel-based regenerative scaffold for chronic nerve interfacing in amputees, 2015, 151-165, v41, Biomaterials, USA.
Monica Friedlander, Neural implants come of age, S&TR Jun. 2012, 20-23, Lawrence Livermore National Laboratory, USA.
Washington University in St. Louis, Device may allow sensation in prosthetic hands, May 13, 2015, 1-3, http://phys.org/news/2015-05-device-sensations-prosthetic.html.
Richard Barrett et al., Spiral peripheral nerve interface; updated fabrication process of the regenerative implant, Jul. 2013, 771-774, 35th Ann. Int. Conf. of IEEE EMBS, Jap.
Zachary P. French el al., Complete regenerative peripheral nerve interfaces, fatigue and recovery, 2015, (No. pp. Nos.), Section of Plastic Surgery, U of Michigan.
Bao Tram Nghiem et al., Providing a sense of touch to prosthetic hands, 2015, 1652-1663, v135, No. 6, American Society of Plastic Surgeons, USA.

* cited by examiner

ANNULAR ELECTRODE ARRAY

CROSS-REFERENCE TO RELATED APPLICATIONS

Not applicable

BACKGROUND

Field of Invention

The present invention relates generally to a three-dimensional electrode array and more particularly to an implantable three-dimensional annular electrode array (AEA) comprised of electrode sub-array nodes presenting electrode terminals that are captured and sequestered by regenerating nerve axons. The apparatus is adapted for chronic implantation between the proximal and distal ends of a transected nerve, respectively, or nerve stump. The disclosed device may particularly be useful as a neural interface to detect afferent and efferent signals for the neural control of external and internal electromechanical devices and transduction of feedback stimuli from these devices for relay to the nervous system.

Three of the current technologies used for nerve stimulation and recording are (1) microelectrode arrays; (2) sieve electrodes and (3) intraneural electrodes. Each of these technologies suffers serious inherent technical problems and associated detrimental biological complications.

Two examples of penetrating microelectrode arrays are: 2D arrays in which the tips of the electrodes are on the same plane, which in: US005215088A to Norman et al. (2005) is claimed as a 3D electrode array, and 3D arrays called slanted arrays, because the tips of the electrodes are on different planes. Both the 2D and the 3D Utah Slanted Electrode Array (USEA) have not been used chronically for either stimulation or recording in peripheral nerve and the biological effects of the surgical technique highly affects long-term stimulation results.

Implantation of this device requires a complex apparatus that physically impales the sharp needle-like electrodes in the array into nervous tissue, causing significant mechanical damage, cell death, disruption of nerve axons, an immediate inflammatory response form the host and subsequent scar tissue formation around the electrodes, leading to a loss of signal detection or ability to stimulate the nerve fibers.

Other critical issues associated with chronic implantation of a 2D or 3D USEA microelectrode array include the substantial relative motion between the nerve and surrounding muscles; which would exert forces on the electrode array and eventually extract it from the nerve. The nerve could also suffer mechanical damage due to the electrodes rigidity which would not allow it to move with the nerve. To date, an efficient system required to keep the electrodes within the nerve is not available.

Additional complications arise from tensional forces on the USEA electrode array lead generated by movement, causing the array to dislodge or shift from its original position. Anchoring of these arrays is on the nerve surface, making it difficult to secure in place. A critical limitation on the maximum size of the electrode array that can be used is due to the geometry of the construct, which is square or rectangular, intended for implantation onto a cylindrical nerve. A further limitation is related to the number and proximity to each other of electrodes in the arrays: an increase in the number and proximity of electrodes is directly correlated to an increase in the resistance of the tissue to penetration, thus increasing the ability and difficulty of implantation.

A third example of a penetrating electrode array is the intraneural electrode, claimed in US007603153B2 to Jacobson et al. (2009). With intraneural electrodes, recording and stimulation is not specific due to the spatial distribution of the nodes of Ranvier along a peripheral nerve axon. Furthermore, the intraneural electrodes may not be in the proper position in order to record or stimulate; it may miss the target nerve axon population entirely. Additionally, trauma caused by electrode penetration induces acute, late, and chronic foreign body inflammatory response by the host.

Another type of electrode array described in the prior art, are sieve electrodes, US6908470B2 to Stieglitz et al. (2005). Major drawbacks associated with sieve electrodes are: a difficulty to establish long-term connections to devices and only a small percentage of the nerve cross-sectional area is open for regeneration through the substrate. Furthermore, the leads also produce tethering forces that could result in (1) movement of the electrode from its original position; (2) electrode extraction; (3) tissue damage due to the blade-like geometry of the substrate and sharp edges associated with each hole of the sieve through which the nerve fibres must cross; (4) fibrotic scar tissue development around the implant due to surgical trauma leading to loss of signal; and (5) implanting of the sieve electrode at the nerve stump is not an optimal position for placement.

In summary, complications associated with penetrating and sieve electrodes implantation are: (1) focal nerve fibre compression and demyelination; (2) post-surgical edema; (3) seroma formation; (4) fibrous encapsulation of the implant (the fibrotic capsule may lead to displacement of the electrode positions and changes in tissue impedance; (5) scar tissue formation at the surgical site; (6) scar tissue formation around the microelectrodes and subsequent signal loss; and (7) excessive tension in the electrode leads results in shifting or extraction of the array from its original position.

BRIEF SUMMARY OF THE INVENTION

My invention is a three-dimensional annular electrode array that provides the electrical and mechanical structural elements necessary to establish a bio-electromechanical interface capable of detecting afferent and efferent signals for the neural control and sensory feedback of bionic devices.

Attempts are being made to achieve the neural control of bionic prosthetic devices. Significant advances in robotics, nano- and micro-fabrication, computing and software development have been made that can be applied to this end.

A critical limiting factor is the neural interface. The prior art does not provide the electrode array architecture to meet the requirements that would provide a high resolution, stable, long-term interface between a biological system and electromechanical systems.

My three-dimensional annular electrode array overcomes the many limiting factors and drawbacks inherent of the prior art. The novel architecture of the disclosed invention has the potential to meet the requirements needed to provide a high resolution, stable, biocompatible, long-term interface between a biological system and electromechanical systems.

Objects and Advantages

Accordingly, besides the objects and advantages of the annular electrode array described in my above patent, several objects and advantages of the present invention are:

(a) it can be coupled to the proximal and distal ends of a transected nerve, respectively, providing an optimal environment for axon regeneration;
(b) it eliminates the need for a specialized device for implantation;
(c) it reduces the time required for surgical implantation;
(d) it minimizes surgical risk to the subject;
(e) it attaches easily and securely to a sleeve or directly to a nerve;
(f) it provides an efficient system to maintain electrode contact with nerve tissue;
(g) it establishes a continuity of nerve tissue between the proximal and distal nerve stumps of a transected nerve;
(h) it becomes assimilated by regenerated nerve tissue;
(i) it provides protection from mechanical damage for the electrode arrays;
(j) it is comprised of electrode sub-arrays that do not cause acute tissue damage;
(k) it prevents tissue damage due to electrode micro-movement;
(l) it prevents electrode shifting or dislodging during normal movements;
(m) it provides electrode terminals that are captured and sequestered by regenerating nerve axons;
(n) it eliminates neural signal "cross-talk" by providing the necessary distance between electrodes;
(o) it establishes a long-term connection between an electrode terminal contact and regenerated nerve axons;
(p) it provides for updating of external systems without disturbing the contact between regenerated nerve axons and the electrode terminal;
(q) it allows signal sampling form individual electrodes for processing, modulation, amplification, direction, and specific targeting;
(r) it has both motor and sensory signal detection capabilities by providing for selecting of the modality of the neural signal at the electrode interface with regenerated nerve axons.

To maintain long-term biocompatibility, the three-dimensional annular electrode array is constructed with FDA-approved polymer materials which include polymethylmethacrylate (PMMA—used in intraocular lenses), polydimethylsiloxane (PDMS—form of silicone used in many implants), polytetrafluoroethylene (PTFE—common chemical name for TEFLON®), parylene (currently used to coat neural probes and cochlear implant electrodes), and biocompatible forms of polyurethane or polycarbonate. Electrodes are in the form of an insulated microwire with a core comprised of a conducting material, preferably carbon nanotube yarn, but can include other presentations of carbon nanotubes, and conducting metals and their alloys.

BRIEF DESCRIPTION OF THE SEVERAL VIEWS OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, can be arranged and designed in a wide variety of different configurations. Nonetheless, the invention will be described and explained with additional specificity and detail through the use of the accompanying drawings in which:

REFERENCE NUMERALS IN DRAWINGS

Figure 1:
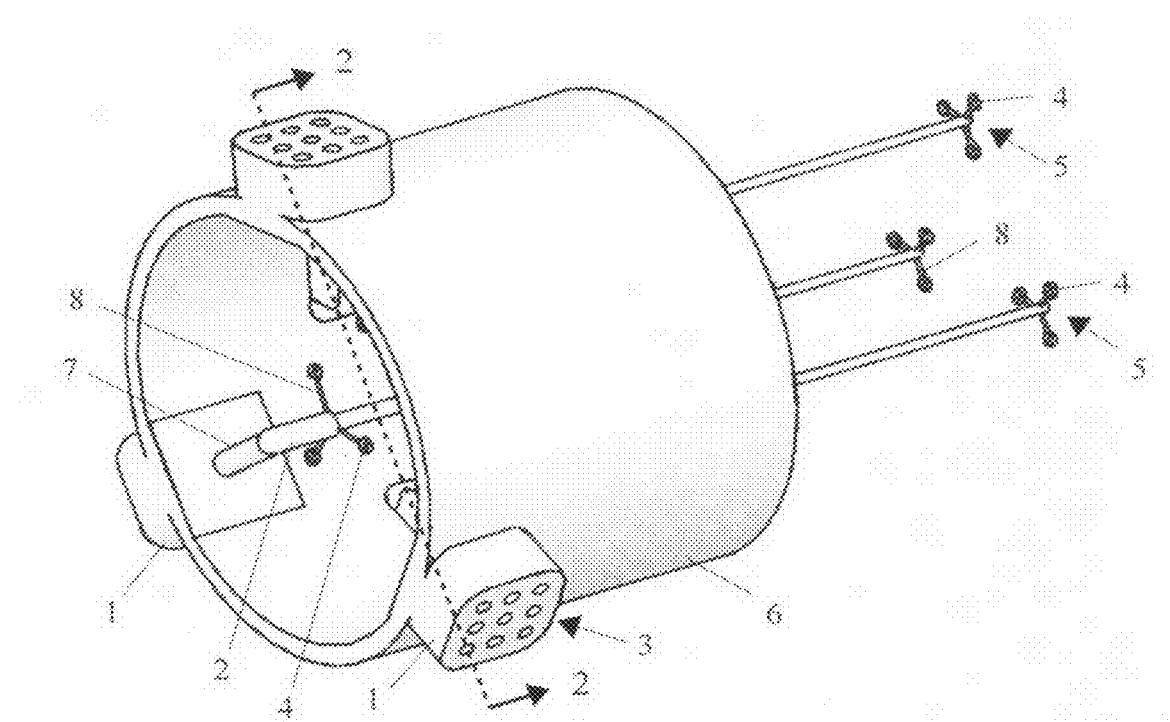
FIG. 1 illustrates a perspective view of a three-dimensional annular electrode array.

1. Connector
2. Electrode sub-array node
3. Connector contact array
4. Electrode terminal
5. Electrode cluster
6. Annular electrode array body
7. Primary electrode lead
8. Electrode microwire
9. Distal extension sleeve
10. Proximal extension sleeve
11. Compartment
12. Compartmentalized inner core

DETAILED DESCRIPTION OF THE INVENTION

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

In describing the present invention, the following terminology will be used: the singular forms of "a", "an", and "the" include plural referents unless the context clearly dictates otherwise. Thus, for example, reference to an electrode includes reference to one or more electrodes.

As used herein, the term "about" means quantities, dimensions, sizes, formulations, parameters, shapes and other characteristics need not be exact, but may be approximated and/or larger or smaller, as described, reflecting acceptable tolerances, conversion factors, rounding off, measurement error and the like and other factors known to those of skill in the art.

Numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values of sub-ranges encompassed within that range as if each numerical value and sub-range is explicitly recited. As an illustration, a numerical range of "about 1 to 5" should be interpreted to include not only the explicitly recited values of about 1 to 5, but also include individual values and sub-ranges within the indicated range. Thus, included in this numerical range are individual values such as 2, 3, and 4 and sub-ranges such as 1-3, 2-4, and 3-5, etc. This same principal applies to ranges reciting only one numerical value and should apply regardless of the breadth of the range or the characteristics being described.

As used herein, a plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "electrode", "electrode terminal", or "micro-electrode" are used interchangeably and means an electric conductor through which a voltage potential can be measured. An electrode can also be a collector and/or emitter of an electric current. Preferably, an electrode is an insulated microwire wherein said microwire core is comprised of a conducting material, preferably carbon nanotube yarn, including other presentations of carbon nanotubes, and conducting metals and their alloys. The term "electrode" can also describe a collection of microwires. Thus, particularly preferred electrodes comprise carbon nanotube yarn microwires coated with material selected from the group consisting of S-Isonel, polymers, plastics, nonconductive materials, parylene C, F, M, A, AM, N or D, of these, particularly preferred are parylene C or polytetrafluoroethylene (PTFE) TEFLON®.

As used herein, the term "microwire" means a uniformly insulated conductive wire having a diameter of between about 10 μm and 75 μm.

As used herein, the term "electrode cluster" means a collection of two or more electrodes electrically insulated from other electrodes in the array, having a first and a second end. The first end of an electrode is preferably, but not required to be, adapted to interact with neural tissue and the second end is preferably disposed in electrical communication with external electromechanical devices. Preferably the second end of each electrode is in a fixed spatial relationship with other electrodes of the micro-electrode arrays in one or more contacts in a connector.

As used herein, "group", "cluster" and "array" are used interchangeably and mean a plurality of electrodes.

As used herein, "node" and "electrode sub-array node" are used interchangeably and mean a plurality of bundled microwires to form an electrode sub-array.

As used herein, the terms "actuator", "external device", "prosthetic limb", "brain-machine interface", and "exoskeleton" are used interchangeably and mean any kind of device adapted to perform a movement. Although an actuator preferably performs a movement in three dimensions, an actuator can also be limited to performing movements in two dimensions. A preferred actuator comprises a prosthetic limb, which can be fitted on, or integrated into, the body of a subject. An actuator can also be associated with machinery and/or electronic circuitry that allow the actuator to respond to one or more forms of input with one or more movements. It is also preferable that the range of motion of an actuator designated as a substitute for a patients lost or paralyzed limb not be limited to the range of motion for which the actuator is substituting.

As used herein, the term "signal" or "neural signal" means a signal, which can take any form, originating in the nervous system of an organism or an external device.

As used herein, the terms "annular electrode array", "AEA", "three-dimensional annular electrode array", "implant", "cybernetic neural interface", cybernetic bio-interface" and "device" are used interchangeably and mean the disclosed invention, unless the context dictates otherwise.

As used herein, the term "nerve stimulator" means any device or means adapted to stimulate one or more nerves. Stimulation imparted by a nerve stimulator can be of an electrical, optical, chemical or physical nature, however electrical stimulation is preferred.

A three-dimensional annular electrode array can be connected to active electronics that can include amplifiers, attenuators, multiplexers, demultiplexers, wireless transmitters, wireless receivers, wireless transceivers, and the like. For example, multiplexers and demultiplexers can be used to combine multiple signals for input and output from the electrode.

As yet another example, the active electronic circuitry can include a wireless or wired transmitter and receiver. For example, electrodes within the annular electrode array can be integrated via the connector with a wireless transmitter and receiver and power source, and be entirely or partially contained subcutaneously, intra-muscularly or intra-osseously.

As used herein, "assimilated" means the act or process of "implant incorporation", "appropriation" or "taking in" by the tissue, thus, becoming a part of a biological system.

With reference to FIG. 1, shown is an illustration of a three-dimensional annular electrode array, according to the first exemplary embodiment of the present invention. Specifically, FIG. 1 shows a perspective view of a three-dimensional annular electrode array with an outer diameter of about 3 mm, an internal diameter of about 2.760 mm and a length of about 2.50 mm, comprised of a plurality of connectors 1 of about 0.750 mm wide by about 0.750 long by about 0.380 mm high, showing a connector contact array 3 with about nine contact ports of about 0.10 mm in diameter spaced approximately 0.20 mm center-to-center. A primary electrode lead 7 of about 0.180 mm in diameter comprised of bundled individually insulated electrode microwires, extends laterally approximately 0.60 mm from the base of the connector 1, bending at an angle of approximately 90°, to form an electrode sub-array node 2 with an initial diameter of about 0.180 mm and a diameter of about 0.050 mm at its terminal end extending into the lumen of an annular electrode array body 6 oriented in parallel with respect to its longitudinal axis.

Figure 2:
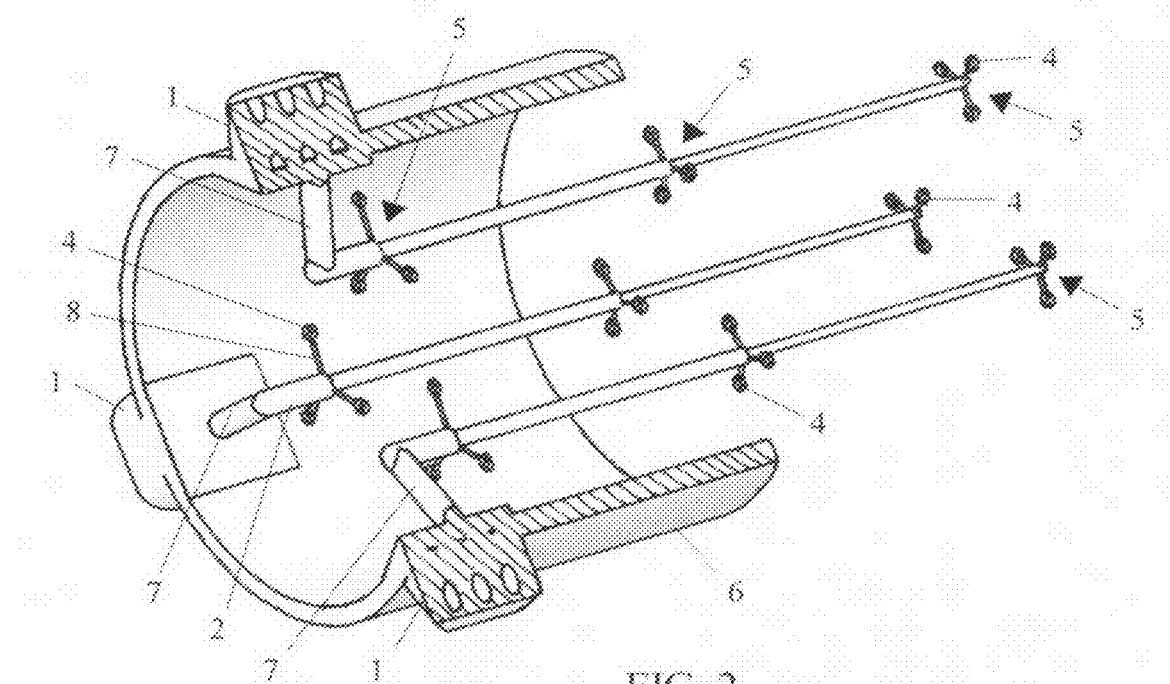
FIG. 2 illustrates a lateral sectional view of a three-dimensional annular electrode array.

FIG. 2 illustrates a sectional view of an annular electrode array showing approximately three electrode sub-array nodes 2, spaced approximately at 120° from each other, comprised of a plurality of radially positioned electrode terminals 4 projecting laterally from about 0.010 mm to about 0.50 mm with relation to the longitudinal axis of the node, preferably terminating in a forward-facing loop of approximately 0.10 mm in outer diameter and approximately 0.080 mm internal diameter, forming an electrode cluster 5 comprised of about three electrode terminals 4 with a distance of about 2 mm separating each cluster along the length of the node.

Figure 3:
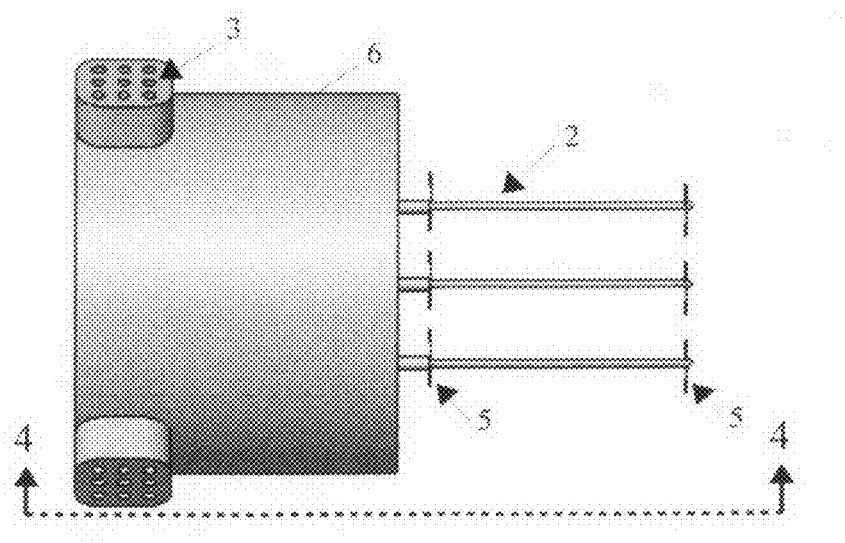
FIG. 3 illustrates a lateral view of a three-dimensional annular electrode array.

FIG. 3 illustrates a lateral view of an annular electrode array showing a side view of an AEA body with a plurality of electrode sub-array nodes 2 comprised of electrode clusters 5 comprised of electrode terminals 4.

Figure 4:
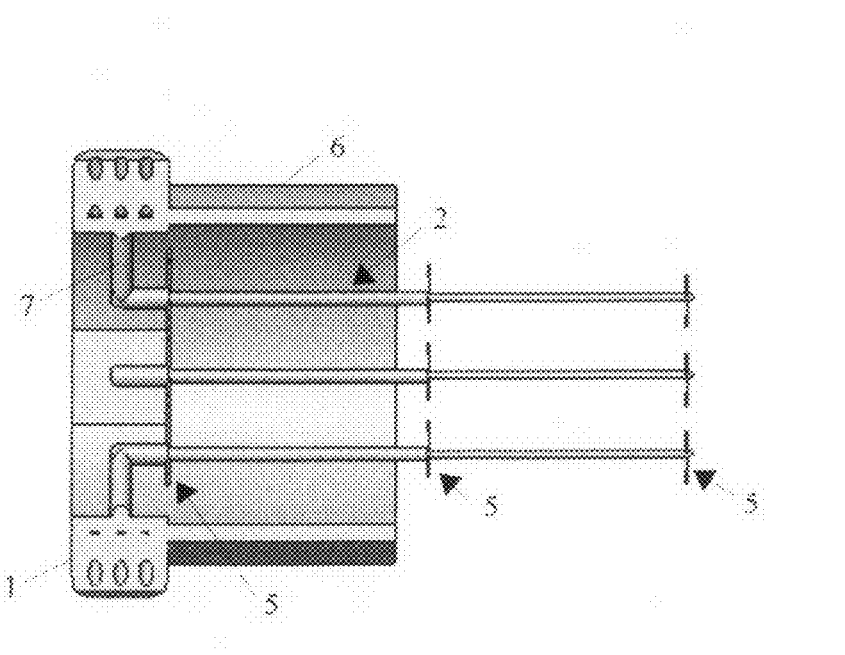
FIG. 4 illustrates a lateral sectional view of a three-dimensional annular electrode array.

FIG. 4 illustrates a lateral sectional view of a three-dimensional annular electrode array showing a primary electrode lead 7 extending from a connector 1 and bending in an angle of about 90° to form an electrode sub-array node 2.

Figure 5:
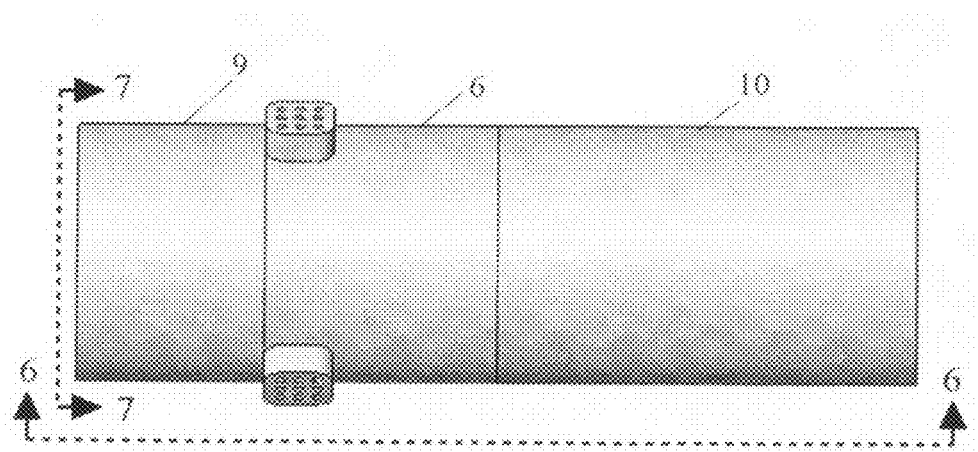
FIG. 5 illustrates a lateral view of a three-dimensional annular electrode array with sleeves coupled to its proximal and distal ends, respectively.

FIG. 5 illustrates a lateral view of a distal sleeve extension 9 of about 2 mm in length with an external diameter of about 3 mm and an internal diameter of about 2.760 mm and a proximal sleeve extension 10 of about 4.50 mm in length with an external diameter of about 3 mm and an internal diameter of about 2.760 mm coupled to a first end and a second end of an AEA body 6, respectively.

Figure 6:
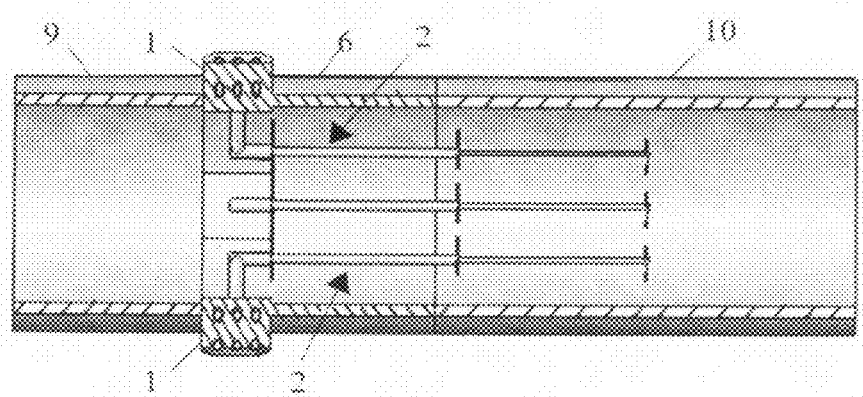
FIG. 6 illustrates a sectional lateral view of a three-dimensional annular electrode array with sleeves coupled to its proximal and distal ends, respectively.

FIG. 6 illustrates a lateral sectional view showing a preferred embodiment of about three sub-array nodes 2 in an AEA coupled to distal and proximal sleeve extensions, respectively.

Figure 7:
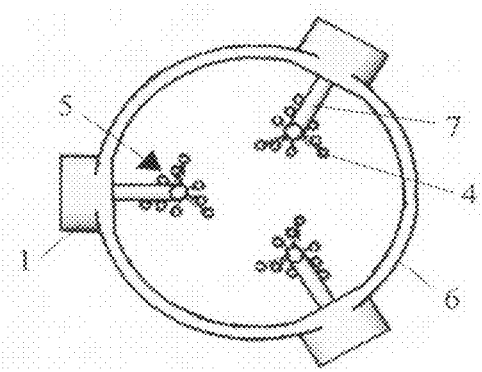
FIG. 7 illustrates a rear view of a three-dimensional annular electrode array.

FIG. 7 illustrates a rear view of an AEA showing a plurality of electrode terminals 4 with a preferred embodiment of forward-facing loops, extending laterally from electrode clusters 2, radiating out at variable distances about the node (not visible).

Figure 8:
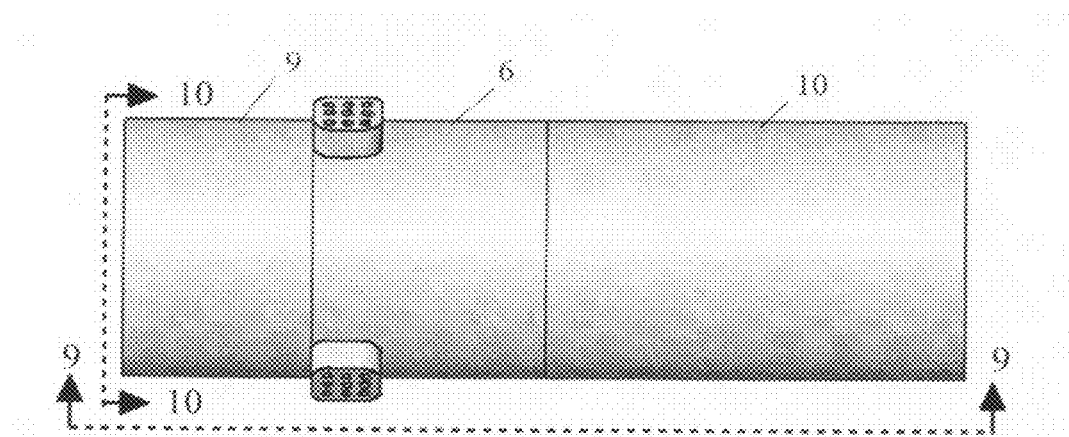
FIG. 8 illustrates a lateral view of a three-dimensional annular electrode array with sleeves coupled to its proximal and distal ends, respectively.

FIG. 8 illustrates a lateral view of an AEA coupled to a distal 9 and proximal 10 sleeve extensions, respectively.

Figure 9:
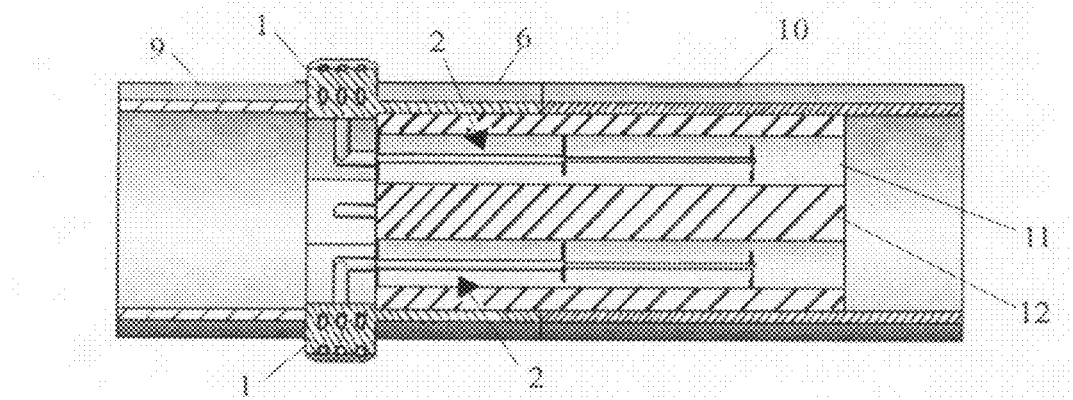
FIG. 9 illustrates a sectional lateral view of a three-dimensional annular electrode array with sleeves coupled to its proximal and distal ends, respectively, and a compartmentalized inner core.

FIG. 9 illustrates a lateral sectional view showing an AEA coupled to distal and proximal sleeve extensions, respectively, with an internal compartmentalized core 12 of about 5 mm in length by about 2.75 mm in diameter housing an electrode sub-array node within a compartment 11 of approximately 5 mm in length by about 1 mm in diameter, open at its first and second end.

Figure 10:
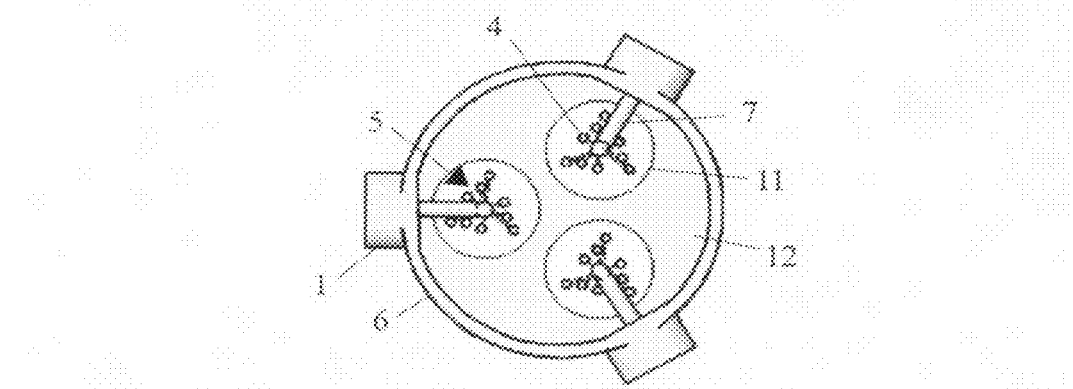
FIG. 10 illustrates a rear view of a three-dimensional annular electrode array and a compartmentalized inner core.

FIG. 10 illustrates a rear view of an AEA showing a plurality of electrode terminals 4 with a preferred embodiment of a forward-facing loop, extending laterally from electrode clusters 5, radiating out at preselected distances about the node (not visible) housed within a compartment 11 of a compartmentalized core 12.

Operation of the Invention—FIGS. 5-10

The annular electrode array operates as a cybernetic neural interface for the control and sensory feedback of a robotic prosthetic device. This is achieved in preferred embodiments by coupling the AEA to an open sleeve 9, 10, shown in FIGS. 5-7, or to a sleeve containing a compartmentalized core 12 to separately house an individual electrode sub-array node 2, shown in FIGS. 8-10, and inserting and securing, for example: by suture or bio-glue, the proximal and distal ends of a transected nerve into the proximal and distal ends of the sleeves 9, 10, respectively, coupled to the AEA. Continuity of the open sleeve or compartment in a sleeve containing a compartmentalized core 12, is because the open space is only partially occupied by a node(s) 2. This allows tissue, preferably regenerating nerve axons, to enter, extend, and populate the interior of the compartment from both the proximal and distal directions. As the tissue regenerates, a number of regenerating nerve axons enter through the loops of the electrode terminals.

The forward-facing loop at the end of laterally positioned radiating electrode terminals 4 about the node 2 is designed to be captured and sequestered by regenerating nerve axons in three-dimensions. The regenerated nerve axons form a fascicle, comprised of a number of motor and sensory axons within the loop, thus establishing a stable long-term interface with the electrode contact, for the transmission or transduction of a neural signal to a wired or wireless device. The distribution of laterally radiating electrode clusters 5 along the length of the node 2 provide the ability for regenerating nerve axons to capture and sequester electrode terminals at multiple levels with respect to the X, Y, Z axis'.

Electrodes are made of a preselected length of microwire, preferably comprised of carbon nanotube yarn, of approximately 0.005 mm to about 0.075 mm in diameter and a length of about 2-15 mm, preferably insulated with parylene or TEFLON®. The second end of the microwire 8 is wrapped around a projecting micro-pin of a diameter of about 0.10 mm, secured in a base, to form an electrode terminal loop 4 of approximately 0.10 mm in diameter followed by bending the terminal end of the microwire into the opening of the loop and securing to the microwire using an adhesive, for example epoxy. The resulting electrode is then lifted from the micro-pin for assembly of the primary electrode lead 7 and node 2. The exposed electrically conducting core of the end of the micro wire 8 positioned within the opening of the loop provides a point of contact with nerve axons that regenerate through the loop for signal transmission or detection.

A preferred method for producing the electrodes is comprises of taking a preselected length of uninsulated microwire of the dimensions described above. A loop is produced in the second end as previously described and secured by way of an adhesive as described or, alternatively, it can be secured by tieing a knot around the lead. The electrodes containing a loop are then insulated by a preferred process of chemical vapor deposition using, for example, parylene. Once insulated, a preselected area within the internal face of the loop is de-insulated, preferably by use of a laser, to provide a point of contact with regenerated nerve axons that occupy the loop for signal transmission or detection; establishing a long-term, stable, high resolution, highly sensitive interface between the nerve axons and the point of contact within the wall of the electrode loop.

An electrode sub-array node 2 is produced by arranging and securing variable lengths of electrode microwires into a bundle and peeling a length of about 0.050 to about 0.40 mm of the electrode terminal at its first end back to an angle approximately perpendicular to the central axis of the node so that the loop opening is facing forward, thus forming an electrode cluster 5 radiating out approximately 0.050 to about 0.40 mm about the central axis of the node.

The level of each cluster on the node is a result of the different lengths of the microwires that make up the node at that point. The diameter of a node 2 is greater at its second end, decreasing progressively towards its terminal first end because the sum of the diameters of the microwires at the level of each electrode cluster 5 decreases; this gives the node a greater degree of flexibility to prevent tissue damage due to micro-movement.

The primary electrode lead 7 is formed by bending the second end of the electrode microwire 8 bundle about 90° for connection of the second end of the individual electrodes to their respective contacts within the connector 1 of the AEA body, fabricated by known methods for production of electrical components.

It is clear to one skilled in the art that regenerating nerve tissue through the lumen of the AEA, containing the electrode sub-array node 2, enters through and surrounds the loops of the plurality of radiating electrode terminals 4 and electrode clusters 5, thus, anchoring the electrode sub-array node(s) 2 and electrode terminals 4 within the regenerated nerve tissue. Thus, the AEA implant is assimilated into the host system; this provides the advantages of preventing acute tissue damage, inflammation, scar tissue formation, tissue compression, electrode micro-movement, shifting, or extraction due to tethering forces at the connectors and loss of signal associated with the electrode arrays described in the prior art.

Conclusions, Ramifications, and Scope

The present invention has been described in accordance with several exemplary embodiments, which are intended to be illustrative in all aspects, rather than restrictive. Thus the present invention is capable of many variations in detailed implementation, which may be derived from the description contained herein by a person of ordinary skill in the art.

For example, the primary electrode lead 7 can branch into more than one electrode sub-array node 2; the length of the electrode sub-array node 2 can be increased or decreased; the connector 1 can be substituted by a preferred hermetically-sealing, high density connector to prevent exposure of the internal connector contacts with the host, entry of moisture, and to greatly increase the number of electrodes that can be built into the AEA; the compartmentalized core 12 can be comprised of a bio-compatible biopolymer such as agarose, collagen, a micro-porous gel, extracellular matrix, a precast micro-fibers insert or combinations of these; the ends of the AEA body 6 can be lengthened or shortened; the diameter of the AEA can be increased or decreased; the number of electrodes in each electrode cluster 5 can be increased or decreased; the diameter and length of the inner core can be increased or decreased; the number, length, and diameter of compartments 11 can be increased or decreased; extending the electrode microwire 8 first end into the terminal loop 4 opening allows for nerve axon stimulation and signal detection from within a regenerated nerve fascicle; the electrode terminals extending laterally from the node can be fabricated without a terminal loop; the electrode terminals extending laterally from the node can be positioned randomly about the node; an electromagnetic interference shield can be incorporated into the material of the AEA body; the AEA body can incorporate perforations to easily secure it to the ends of a transected nerve using sutures, etc.

Thus, the scope of the invention should be determined by the appended claims and their legal equivalents, rather than by the example given.

I claim:
1. A nerve interfacing device comprising:
   a. a body (6) comprising:
      i. an element for attachment to a nerve or attachment to an element that attaches to a nerve; and
      ii. a connector (1) for attachment of a primary electrode lead (7) of one or more electrode sub-array nodes (2); and
      iii. one or more wires that connect to the electrode sub-array node (2), wherein each of the wires comprises one or more electrode clusters (5) separated by an internode, wherein each of the electrode clusters (5) comprises:
      iv. one or more electrode micro-wires (8) comprising:
         1. a first end to attach to the electrode sub-array node (2) that connects to the connector (1) which connects to one or more external systems that control input and output to and from the electrode microwires (8); and
         2. a second end including an electrode terminal (4) that interfaces with the nerve tissue via a point of contact to provide electrical stimulation and detect nerve signals, wherein the one or more electrode micro-wires (8) are disposed radially, furcating outwards laterally at an angle of between 1-90 degrees inclusively with relation to a longitudinal axis of the electrode sub-array node (2), and wherein the one or more electrode micro-wires (8) have a diameter of between 0.0001-10 millimeters inclusively; and the one or more electrode micro-wires (8) have a length of between 1-100 millimeters inclusively
   b. a three dimensional electrode array comprising a hierarchical, modular, multiaxial device.

2. The nerve interfacing device of claim 1 wherein the body (6) is in a shape selected from: an annulus; an oval; a square; a rectangle; an elongated, hollow, cylindrical tube or a multi-luminal elongated tube.

3. The nerve interfacing device of claim 1 wherein the body (6) is comprised of a diameter of between 1-30 millimeters inclusively and a length of between 1-60 millimeters inclusively.

4. The nerve interfacing device of claim 1 wherein the body (6) is comprised of a material selected from a group of biocompatible materials consisting of polyurethane, polycarbonate, polydimethylsiloxane, polypropylene, polytetrafluoroethylene, polymethylmethacrylate, poly(etherketoneketone) PEEK, poly(vinyl chloride) PVC, polyethylene, PEI (polyetherimide) and polysulfone.

5. The nerve interfacing device of claim 1 wherein the body (6) includes the connector (1) to house the plurality of electrode micro-wires (8) first-ends of a primary electrode lead (7) for interfacing to selected external systems.

6. The nerve interfacing device of claim 1 wherein the one or more electrode micro-wires (8) are comprised of a length of between 1-60 millimeters inclusively and a diameter of between 1-30 millimeters inclusively, with a second end comprising an electrode terminal (4) furcating outward radially comprising an arm disposed at an angle of between 1-90 degrees inclusively with relation to the longitudinal axis of the electrode sub-array node (2) to interface with nerve tissue.

7. The nerve interfacing device of claim 1 wherein the electrode micro-wires (8) further includes an electrode terminal (4) in a shape selected from: a loop, an oval, a triangle, and a square of between 1-500 microns inclusively to interface with nerve tissue.

8. The nerve interfacing device of claim 7 wherein the electrode terminal (4) is annular.

9. The nerve interfacing device of claim 1 wherein the one or more electrode micro-wires (8) comprise a material selected from a group of materials consisting of conductive alloys, conductive polymers, stainless steel, noble metals, tungsten, graphene and carbon nanotubes.

10. The nerve interfacing device of claim 9 wherein the one or more electrode micro-wires (8) are coated with one or more of an insulating material selected from the group consisting of parylene, polymers, plastics, polytetrafluoroethylene (PTFE) and non-conductive materials.

11. The nerve interfacing device of claim 1 wherein the one or more electrode micro-wires (8) electrode terminals (4) comprise the electrode cluster (5).

12. The nerve interfacing device of claim 1 wherein the one or more electrode micro-wire (8) comprises electrode terminals (4) in the electrode cluster (5) and wherein a primary electrode lead (7) and the electrode cluster (5) comprise the electrode sub-array node (2).

13. The nerve interfacing device of claim 12 wherein the one or more electrode clusters (5) of the one or more electrode sub-array nodes (2) comprises:
  a. the electrode cluster (5) is separated from the adjacent electrode cluster (5) by an internode of a length between 0.01-10 millimeters inclusively comprising the electrode sub-array nodes (2);
  b. wherein a portion of the electrode micro-wires (8) are of equal length; and
  c. a separate portion of the electrode micro-wires (8) are of unequal length;
  d. the electrode cluster (5) is comprised of a greater number of the electrode micro-wires (8) than the number of the plurality of electrode micro-wires (8) of the adjacent electrode cluster (5); and
  e. the plurality of electrode micro-wires (8) furcate outward radially at a greater distance from the longitudinal axis of the electrode sub-array node (2) than the adjacent electrode cluster (5) separated by an internode.

14. The nerve interfacing device of claim 1 wherein the one or more electrode clusters (5) are defined further as comprising:
  a. a first-order three-dimensional electrode array comprising:
    i. the electrode sub-array node (2) is comprised of the electrode clusters (5) furcating outwards radially about an x, y and z axis disposed along a longitudinal axis of a primary electrode lead separated by internodes (7);
  b. a second-order three-dimensional electrode array comprising:
    i. the electrode lead furcating outwards radially about an x, y and z axis to comprise a plurality of electrode sub-array nodes (2); and
  c. a third-order three-dimensional electrode array comprising:
    i. the electrode sub-array nodes (2) wherein the electrode sub-array nodes (2) further comprises a module; and
    ii. the modules are disposed radially about an x, y and z axis.

\* \* \* \* \*